United States Patent [19]
Kaestle

[11] Patent Number: 5,800,348
[45] Date of Patent: Sep. 1, 1998

[54] APPARATUS AND METHOD FOR MEDICAL MONITORING, IN PARTICULAR PULSE OXIMETER

[75] Inventor: Siegfried Kaestle, Nufringen, Germany

[73] Assignee: Hewlett-Packard Company, Palo Alto, Calif.

[21] Appl. No.: 710,794

[22] Filed: Sep. 23, 1996

Related U.S. Application Data

[63] Continuation-in-part of Ser. No. 565,879, Dec. 1, 1995, abandoned.

[30] Foreign Application Priority Data

Aug. 31, 1995 [EP] European Pat. Off. ............ 95113654
Aug. 6, 1996 [EP] European Pat. Off. ............ 96112658

[51] Int. Cl.⁶ .................................................. A61B 5/00
[52] U.S. Cl. ..................... 600/322; 600/323; 600/336
[58] Field of Search ........................ 128/633, 664–7, 128/719; 356/39–41; 600/322, 323, 336, 339, 340, 341, 473, 476, 478, 479

[56] References Cited

U.S. PATENT DOCUMENTS

| | | |
|---|---|---|
| 4,867,571 | 9/1989 | Frick et al. ............................ 128/633 |
| 5,158,082 | 10/1992 | Jones . |
| 5,349,953 | 9/1994 | McCarthy et al. . |

FOREIGN PATENT DOCUMENTS

| | | |
|---|---|---|
| 0102816A3 | 8/1983 | European Pat. Off. . |
| 0502717A1 | 3/1992 | European Pat. Off. . |

Primary Examiner—Jennifer Bahr
Assistant Examiner—Bryan K. Yarnell

[57] ABSTRACT

A method for measuring medical parameters of a patient by radiation of electromagnetic waves into a sample and for measurement and subsequent analysis of the electromagnetic waves which have passed through the sample, the following steps are carried out. First and second modulation signals are generated having equal frequencies and a first phase difference of substantially 90°. Irradiating a first electromagnetic wave of a first wavelength into the sample, under control of the first modulation signal. Irradiating the sample with a second electromagnetic wave of a second wavelength, under control of the second modulation signal. Receiving electromagnetic waves of both wavelengths which have passed through the sample and demodulating the received signals by multiplying the same with a first sinusoidal demodulation signal and with a second sinusoidal demodulation signal having the first phase difference with respect to the first sinusoidal signal, the first and second sinusoidal demodulation signals having the same frequency as the first and second modulation signals, such as to generate a first and a second demodulated signal. The first and the second sinusoidal demodulated signals are set so as to have a phase difference relative to the first and second modulation signals corresponding to a system phase shift.

77 Claims, 9 Drawing Sheets

APPARATUS AND METHOD FOR MEDICAL MONITORING, IN PARTICULAR PULSE OXIMETER

REFERENCE TO A RELATED APPLICATION

This application is a continuation-in-part application of the U.S. application Ser. No. 08/565,879, filed Dec. 1, 1995, now abandoned.

FIELD OF THE INVENTION

This invention relates to an apparatus for measuring medical parameters of a patient by irradiation of electromagnetic waves into a sample or material and for measurement and subsequent analysis of the electromagnetic waves which have passed through said sample or material, and to a related method. More specifically and in one particular embodiment, the invention relates to the field of pulse oximetry.

DESCRIPTION OF THE PRIOR ART

Optical methods for measuring medical parameters of a patient are well-known in the art. These include, for example, blood flow measurement, measurement of the perfusion, blood gas analysis, infrared gas analyzers etc., and in particular pulse oximetry. What is common to all of these methods is that light of the visible or adjoining spectra (such as infrared), or other electromagnetic waves, are irradiated into the tissue of a patient, into a sample taken from a patient (such as a blood sample) or into air inspired or expired by the patient. The light transmitted through, or reflected by such sample or material is then analyzed for changes of its characteristics, such as absorbance, wavelength etc., in order to determine a medical parameter of interest. It is understood that such methods are not limited to the use of electromagnetic waves of optical nature (i.e., in the visible spectrum), but that they may use other waves in the electromagnetic spectrum as well. Further, such methods may use the in vivo, as well as the in vitro approach, i.e., they may be focused on the analysis of the patient (e.g., its tissue), or on samples taken from a patient.

In order to increase the clarity and comprehensibility of this description, the underlying problems will now be explained by means of one specific example, namely pulse oximetry. However, it is understood that this does by no means limit the scope of the present invention which is, in fact, also applicable for the measurement of other medical parameters.

Pulse oximetry is a non-invasive technique to evaluate the condition of a patient. Usually, a sensor or a probe comprises light emitting means such as light-emitting diodes (LEDs). Two or more of these LEDs with different wavelengths (e.g., red and infrared) may be used. The emitted light is directed into the tissue of the patient, and light receiving means such as photodiodes or phototransistors measure the amount of transmitted or reflected light. In the case of transmission measurement, the transmitter and receiver diodes are arranged opposite to each other with respect to the human tissue, whereas in the case of reflection measurement, they are arranged on the same side of the tissue.

The measured intensity can be used to calculate oxygen saturation in the arterial blood of the patient if measured at least at two wavelengths. The mathematical background therefor, which makes use of Lambert-Beer's law, has been described in sufficient detail in a multiplicity of former publications. See, for example, EP-A-262 778 which contains a rather good breakdown of the theory.

Usually, the sensor detachably connected to the pulse oximeter comprises at least two LEDs emitting light of a wavelength of e.g. 660 nm (Nanometers)—red—and 900 nm-infrared. The intensity of the emitted light can be modulated by the oximeter in that the exciting current of the LEDs is varied. The photocurrent received by the receiving element is measured by the oximeter and used to calculate the oxygen saturation of the arterial blood.

In today's oximeters, a hardware circuit contained in the front-end portion of an appropriate monitor makes use of a time multiplex approach, where the LEDs are switched on and off one after the other (see U.S. Pat. No. 4,407,290; U.S. Pat. No. 4,523,279 or U.S. Pat. No. 3,847,483). The train of pulses usually consists of a minimum of 3 phases: an active red, an active infrared and a dark phase, where the ambient light is measured during the latter phase. Actually, there can be more than 3 phases to allow for more LEDs to be powered in one multiplexing time frame or additional dark phases. The phases are often of similar duration. The modulation frequency (repetition rate of the whole frame) ranges e.g. from 200 Hz to 2 kHz. This frequency should not be mixed up with the frequency of the light emitted by the LED's. In fact, the common modulation method uses pulse trains with pulses of rectangular shape to excite the LEDs, wherein the first pulse excites the red LED, the second pulse the infrared LED, and an interval without excitation is used to measure the ambient light (called "dark phase" in this context).

It has turned out, however, that such known oximeters, although widely used today in clinical practice (simply because they offer a non-invasive technology), provide limited performance only and, in particular, limited measurement accuracy. This happens mainly when sources of interference, such as neon lamps, UV lamps and other emitters of light, influence the optical path between the LEDs and the photoreceiver. The susceptibility of prior art oximeters to such sources of interference has been known by skilled people; however, no attempts have been made so far to evaluate the reasons therefor. In fact, the following considerations (which explain the mechanism of distortion of oximetry signals) reflect already the inventor's thoughts on this problem, which in turn led him to the present invention, and can insofar already be considered as forming a part of, or—to some extent—the basis of the invention.

The frequency spectrum of a time multiplex signal (as described above) at the receiving photo diode consists of a couple of elements. The first is, of course, the spectral line of the LED modulation frequency. Other spectral lines of reduced amplitude appear at the harmonics of the basic modulation frequency, due to the fact that the spectrum of a pulse sequence contains spectral lines at multiples of the pulse repetition frequency. Such harmonics of significant amplitude appear up to an order of several tens.

Further, all spectral lines are not sharp lines, but rather broadened to some extent, such that they cover small bands in the spectrum. This is due to the fact that the signals are further modulated by the variation of the blood pulse (which contains components up to approx. 10 Hertz). This variation of the blood pulse is actually of interest for medical monitoring. Its frequency may be used to derive the patient's heart rate, and its amplitude is actually required to calculate oxygen saturation.

The blood pulse therefore broadens the spectral lines of the modulation frequency and its harmonics for about ±10 Hertz. This is also called "physiological bandwidth", due to its origin in the physiological signal.

The details and drawbacks of the prior art technology will now be discussed with reference to the drawings.

FIG. 1 depicts the essential functional blocks of a prior art oximeter. A microprocessor 1 controls operation of the oxygen saturation parameter. It generates digitally represented pulses for excitation of the LEDs. These are fed, via line 2, to digital-to-analog converter 3 which outputs analog signals of rectangular shape and feeds them, via line 4, to amplifier 5.

Dotted line 6 represents schematically the interface between the monitor and the sensor. That is, line 7 is physically a cable which connects the sensor and the monitor, and all elements left to dotted line 7 are in practice incorporated into the sensor. The sensor contains at least 2 LEDs 8 and 9 which emit light into the tissue of a patient, here a finger 10. Light transmitted through finger 10 reaches photodiode 11 and is fed, via line 12, to another amplifier 13. The amplified analog signal produced by amplifier 13 is fed (line 14) to a demodulation and filter section 14. This demodulation section comprises a demultiplexer 14a which feeds the amplified signal, depending on its time slot, to three different paths 14b to 14d which implement a low-pass/sample and hold function each. Demultiplexer 14a is controlled such that signals received during operation of LED 8 are fed to path 14b, signals received during operation of LED 9 are fed to path 14c, and signals received during the dark or ambient phase (LED's 8 and 9 switched off) are fed to path 14d.

Each of paths 14b to 14d operates as an independent low-pass filter—see, e.g., resistor 14e and capacitor 14f in path 14b—; the capacitor acts insofar also as a sample and hold device. The three paths 14b to 14d are then combined again by multiplexer 14g (which is synchronized with demultiplexer 14a, see dotted line 14h), and the signals are fed to analog-to-digital converter (ADC) 15. This ADC samples the incoming signals, typically once per channel, but a higher sampling rate is also possible. In other words, if a pulse is sent to the red LED 8, it is sensed once by ADC 15 to determine its amplitude, and the variation of the amplitude in succeeding pulse trains reflects pulsatile variation of the arterial blood.

The digitized signal reaches, via line 16, microprocessor 1 which performs the necessary calculations to determine oxygen saturation. The results are then displayed on a display 17.

FIG. 2 is a timing diagram of the pulse train used to excite LEDs 8 and 9. A first pulse 18 controls red LED 8 (FIG. 1), and a second pulse 19 infrared LED 9. When both LEDs have been excited in sequence, a dark phase 20 is provided which is used on the receiver side to measure the amount of ambient light. At $t=T_{LED}$, the whole pattern starts again from the beginning. Thus, the modulation frequency is defined by $$f_{LED} = \frac{1}{T_{LED}} \quad (1)$$

FIGS. 3a to 3c depict the same pattern at the receiver side, separated according to paths 14b to 14d (FIG. 1), i.e., when the pulses have passed the human tissue. FIG. 3a shows the pulse of the red LED 8 (path 14b), FIG. 3b the pulse of the infrared LED 9 (path 14c), and FIG. 3c the signal detected on path 14d (ambient light). One will note that the red and infrared pulses (FIGS. 3a and 3b) are 1. attenuated by a more or less fixed amount which is caused by nonpulsating tissue (DC attenuation);
2. subject to different attenuation in the red and infrared channel, as shown by the different amplitudes of red pulse 21 and infrared pulse 22; and that
3. their amplitudes are modulated with a slow frequency shown by dotted lines 23a and 23b (the frequency is even exaggerated in FIGS. 3a and 3b for the purpose of demonstration), i.e., their amplitudes vary slowly over time. This slow frequency—in the range of 1 to 10 Hertz—reflects the blood pulsation in blood vessels hit by the light emitted by LEDs 8 and 9 and carries the physiological information required to calculate oxygen saturation. It is therefore called "physiological signal", and the associated frequency band "physiological bandwidth". It will also be noted that the superimposed physiological signal has a very small amplitude, as compared to the overall amplitude of the received pulses.

In contrast, the pulse of FIG. 3c which represents ambient light is not modulated by pulsating tissue (ref. no. 23c).

The pulse trains shown in FIGS. 3a to 3c are fed, via multiplexer 14g (FIG. 1), to the input of ADC 15. According to the prior art approach, ADC 15 takes at least one sample of the received pulse at $t=T_1$, $t=T_2$ and $t=T_3$. These samples represent the amplitudes of the red pulse, the infrared pulse and the ambient light, respectively. The technique discussed here corresponds to a demodulation with a rectangular or square wave.

Now let us consider what happens in the frequency domain. FIG. 4 depicts the spectrum of the signal transmitted through the patient's tissue and amplified, but prior to demodulation and sampling, i.e., as it appears on line 14 (FIG. 1). The basic LED modulation frequency $F_{LED}$ is shown as spectral line 24. This is not a "sharp" spectral line. Instead, it is slightly broadened, due to the physiological signal (as discussed above) which in turn modulates the LED signal. The effect is that the LED modulation spectral line appears in fact as a small-band spectrum with a bandwidth of approx. ±10 Hertz around the center of its base frequency.

Reference numbers 24a and 24b designate harmonics of the basic LED modulation frequency, i.e., $2*f_{LED}$ and $3*f_{LED}$. It is understood that these harmonics appear also broadened by the physiological bandwidth, i.e., they are centered at ±10 Hertz around the corresponding harmonic frequency.

In contrast, reference number 25 represents the spectral line of the mains (power line)—at $f_{Line}$—which is the major source of interference; typically, at 50 Hertz (Europe) or 60 Hertz (United States). It is understood that, although the power line has always a specific frequency, this frequency is subject to variations (however small and slow) of the mains frequency. This variability or tolerance band is indicated by dashed box 25'.

The spectrum also contains harmonics of the basic mains frequency $f_{Line}$. These are denoted as 25a through 25g in FIG. 4 and represent frequencies of $2*f_{Line}$ to $8*f_{Line}$ (it will be appreciated that harmonics of even higher order do also exist, but have not been drawn in FIG. 4). Like the basic mains frequency, their harmonics are also spread, see dotted boxes 25a' through 25g'. The diagram shows that the higher the order of the harmonics, the higher the possible variations in frequency.

FIG. 4 reveals also another effect. That is, some of the harmonics of the LED modulation frequency $f_{LED}$, and of the mains frequency $f_{Line}$, are quite close to each other. A typical example is shown by reference number 26. The third order harmonics 24b of the LED modulation frequency, and the seventh order harmonics 25f of the mains frequency, are quite close to each other ($3*f_{LED} \approx 7*f_{Line}$). This means that there is frequent interference in the related bands, in particular in consideration of the broad tolerance band 25f' associated with the seventh order harmonics 25f of the mains frequency. But there are also other doubtful cases, such as indicated by dotted circle 27. Although there is in fact some distance between the second order harmonics 24a of the LED modulation frequency and the fifth order harmonics 25d of the mains frequency, there is still an overlap if we consider the whole tolerance band 25d' associated with $5*f_{Line}$. In other words, if the frequency of the power line deviates slightly from its nominal value, its fifth order harmonic might approach the second order harmonic of the LED modulation frequency, such that there is at least sporadic interference. If we proceed to higher order harmonics, there will always be a danger of interference, just because the tolerance band associated with the harmonics of the mains frequency becomes broader and broader, such that the associated spectra overlap. This is shown by spectra 25e', 25f' and 25g'. It is evident that for these higher frequencies, any harmonic of the LED modulation frequency will necessarily fall into at least one bandwidth of the harmonics of the mains frequency.

One might now ask the question how such interference of the harmonics influences the base band and thus the results of oxygen saturation measurement. The underlying mechanism is demonstrated in FIG. 5.

According to the prior art approach, the received signal is demodulated by demultiplexer 14a. (This kind of demodulation corresponds to synchronous AM demodulation with a square wave, as e.g. described in U.S. Pat. No. 4,807,630). Demodulation with a square wave has the effect that all kinds of difference and sum frequencies—in particular, of the harmonics—appear in the base band close to the signal of interest; i.e., the harmonics are folded down into the base band. This effect is, by way of example, illustrated in FIG. 5. This figure is based on the understanding that the LED sampling frequency is equal to the LED modulation frequency. (Every channel—red, infrared, dark—is separately sampled and demodulated).

However, the harmonics of the mains frequency are only one source of interference which may distort the useful signal for determining oxygen saturation. In a clinical environment, the pulse oximetry sensor picks up ambient light and various electromagnetic noise. The major source for ambient light is room illumination with fluorescence ceiling lamps which gives broad spectral bands with harmonics at harmonics of the power line frequencies, typically 50 Hertz or 60 Hertz. However, electrical noise also comes very often from the power line and shows up as harmonics of the mains frequency. Other well known sources for largely interfering electrical noise are electro-surgery devices used in the operating rooms. They can be very broad-band and at any frequency.

As explained above, the spectra of the signal at multiples of the LED modulation overlap very likely with the spectra of the optical or electrical noise components. Any noise lines in one of the LED modulation bands will be demodulated and intrinsically folded down to the base band and contribute to poor signal-to-noise ratios (S/N). A very dangerous situation for the patient can occur in the monitoring of neonates. These are often treated with very bright UV lamps for the bilirubin photo therapy. As they produce poor signals because of a poor vascular perfusion, the amount of ambient light can cause even situations with a signal-to-noise ratio<1. A pulse oximeter is very likely to be mislead in these situations. It can derive values for pulse rate, oxygen saturation and perfusion index which are wrong because the input signals are dominated by noise instead of patient signals. EP0502717 A1 discloses means and methods for evaluating the concentration of a constituent in an object by measuring the transmission of light of two wavelengths therethrough. First and second light emitters emit light at respective, first and second different wavelengths. A modulator/driver drives the light emitters with respective first and second carriers which vary as a function of time, the carriers being of the same carrier frequency having a phase difference other than 0 and other than an integer multiple of 180°. A detector receives light from the first and second light emitters after the same has passed through the object and generates a resulting detector signal carrying information relating to transmission of the object at both wavelengths. A first demodulated signal which is a sum of a component proportional to the object's transmission at the first wavelength and one or more carrier modulated components is generated by a demodulator from the detector signal in a first channel, whereas a second demodulated signal which is a sum of a component proportional to the object's transmission at the second wavelength and one or more carrier modulated components is generated by the demodulator in a second channel. The carrier modulated components of the signals are filtered out of the first and second channels by a demodulated signal filter.

The demodulator multiplies the detector signal in the first channel with a sinusoidal signal in phase with the first carrier to generate the first demodulated signal, and multiplies the detector signal in the second channel with a sinusoidal signal in phase with the second carrier to generate the second demodulated signal. Therefore, in accordance with the disclosure of EP 0502717 A1, the sinusoidal signal for demodulating the detector signals in the first and the second channel are in phase with the first carrier and the second carrier, respectively. This demodulation method is disadvantageously to the effect that there exists a cross-talking between the first and the second channels, and therefore no accurate evaluation of the concentration of a constituent in an object is possible.

SUMMARY OF THE INVENTION

Starting from this prior art, it is the object of the present invention to provide methods and apparatus for accurately measuring and analysing medical parameters using at least two different electromagnetic waves having different wavelengths, wherein a cross-talking between channels in which received electromagnetic waves of different wavelength are analysed is reduced.

The present invention is based on the perception that in prior art analysis systems for measuring medical parameters, for example the system that is disclosed in EP 0502717 A1, an accurate measurement and subsequent analysis of medical parameters is impossible due to a phase shift which is introduced by the system between the electromagnetic waves which are used to irradiate a sample and the electromagnetic waves which are used for analysis. Therefore, the present invention provides methods and apparatus for measuring medical parameters of a patient by irradiation of electromagnetic waves into a sample and for measurement and subsequent analysis of the electromagnetic waves which have passed through said sample, wherein the system phase shift is compensated during the analysis of the received electromagnetic waves.

In accordance with a first aspect, the above object is achieved by a method for measuring medical parameters of a patient by irridation of electro-magnetic waves into a sample and for measurement and subsequent analysis of the electromagnetic waves which have passed through said sample, said method comprising the steps of:

generating first and second modulation signals of the same frequencies and having a first phase difference of substantially 90°;

irridating a first electromagnetic wave of a first wavelength into said sample under control of said first modulation signal;

irridating a second electromagnetic wave of a second wavelength different from the first one into said sample under control of said second modulation signal;

receiving electromagnetic waves of both wavelengths which have passed through said sample;

demodulating signals repesentative of the received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal;

wherein the first and the second sinusoidal demodulation signals have a phase difference relative to the first and second modulation signals corresponding to a system phase shift; and analysing said demodulated signals.

In accordance with this first aspect of the present invention the first and second sinusoidal demodulation signals comprise a phase difference relative to the first and second modulation signals which corresponds to the system phase shift, whereby the influence of the system phase shift on the result of the analysis is eliminated and therefore a crosstalking between channels is reduced.

In accordance with a second aspect, the above object is achieved by a method for measuring medical parameters of a patient by irridation of electromagnetic waves into a sample and for measurement and subsequent analysis of the electromagnetic waves which have passed through said sample, said method comprising the steps of:

generating first and second modulation signals of the same frequencies and having a first phase difference of substantially 90°;

irridating a first electromagnetic wave of a first wavelength into said sample under control of said first modulation signal;

irridating a second electromagnetic wave of a second wavelength different from the first one into said sample under control of said second modulation signal;

receiving electromagnetic waves of both wavelengths which have passed through said sample;

demodulating signals repesentative of the received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal;

analysing said demodulated signals taking into account a system phase shift.

In accordance with the second aspect of the present invention, demodulating signals of received electromagnetic waves are demodulated by sinusoidal demodulation signals to generate a first and a second demodulated signal. These first and second demodulated signals are analysed, for example by a microprocessor, under consideration of a system phase shift. On the basis of this system phase shift a correction matrix is calculated which is used to correct the demodulated signals in order to eliminate the influence of the system phase shift on the result of the analysis. In accordance with this second aspect of the present invention, the influence of the system phase shift on the result of the analysis can be eliminated by software, for example in the central processing unit of the system.

In accordance with a third aspect, the above object is achieved by a method for measuring medical parameters of a patient by irridation of electromagnetic waves into a sample and for measurement and subsequent analysis of the electromagnetic waves which have passed through said sample, said method comprising the steps of:

generating first and second modulation signals of the same frequencies and having a first phase difference of substantially 90°;

irridating a first electromagnetic wave of a first wavelength into said sample under control of said first modulation signal;

irridating a second electromagnetic wave of a second wavelength different from the first one into said sample under control of said second modulation signal;

receiving electromagnetic waves of both wavelengths which have passed through said sample;

generating delayed received electromagnetic waves by adding a phase shift to the received electromagnetic waves which yields, together with a system phase shift, a total phase shift of the received electromagnetic waves relative to the first and second electromagnetic waves of substantially an integral multiple of 360°;

demodulating signals representative of the delayed received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal; and analysing said demodulated signals.

In accordance with the third aspect of the present invention, the influence of the system phase shift on the result of the analysis is eliminated by adding a phase shift to the received electromagnetic waves, such that a total phase shift of the received electromagnetic waves relative to transmitted electromagnetic waves is substantially an integral multiple of 360°. This total phase shift of an integral multiple of 360° makes sure that a cross-talking between channels of the received electromagnetic waves is reduced.

In accordance with a fourth aspect, the above object is achieved by an apparatus for measuring medical parameters of a patient by irridation of electromagnetic waves into a sample and for measurement and subsequent analysis of the electromagnetic waves which have passed through said sample, said apparatus comprising:

means for generating first and second modulation signals of the same frequencies and having a first phase difference of substantially 90°;

means for irridating a first electromagnetic wave of a first wavelength into said sample under control of said first modulation signal;

means for irridating a second electromagnetic wave of a second wavelength different from the first one into said sample under control of said second modulation signal;

means for receiving electromagnetic waves of both wavelengths which have passed through said sample;

means for demodulating signals repesentative of the received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal;

wherein the first and the second sinusoidal demodulation signals have a phase difference relative to the first and second modulation signals corresponding to a system phase shift; and means for analysing said demodulated signals.

In accordance with a fifth aspect, the above object is achieved by an apparatus for measuring medical parameters of a patient by irridation of electromagnetic waves into a sample and for measurement and subsequent analysis of the electromagnetic waves which have passed through said sample, said method comprising the steps of:

means for generating first and second modulation signals of the same frequencies and having a first phase difference of substantially 90°;

means for irridating a first electromagnetic wave of a first wavelength into said sample under control of said first modulation signal;

means for irridating a second electromagnetic wave of a second wavelength different from the first one into said sample under control of said second modulation signal;

means for receiving electromagnetic waves of both wavelengths which have passed through said sample;

means for demodulating signals repesentative of the received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal; and means for analysing said demodulated signals taking into account a system phase shift.

In accordance with a sixth aspect, the above object is achieved by an apparatus for measuring medical parameters of a patient by irridation of electromagnetic waves into a sample and for measurement and subsequent analysis of the electromagnetic waves which have passed through said sample, said apparatus comprising:

means for generating first and second modulation signals of the same frequencies and having a first phase difference of substantially 90°;

means for irridating a first electromagnetic wave of a first wavelength into said sample under control of said first modulation signal;

means for irridating a second electromagnetic wave of a second wavelength different from the first one into said sample under control of said second modulation signal;

means for receiving electromagnetic waves of both wavelengths which have passed through said sample;

means for generating delayed received electromagnetic waves by adding a phase shift to the received electromagnetic waves which yields, together with a system phase shift, a total phase shift of the received electromagnetic waves relative to the first and second electromagnetic waves of substantially an integral multiple of 360°;

means for demodulating signals representative of the delayed received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal; and means for analysing said demodulated signals.

In accordance with a preferred embodiment of the present invention, the frequency of the modulation signals is determined to be approximately f=275 Hertz. This selection guarantees that the main spectral line of the modulation frequency is placed optimally between harmonics of the noise bands for 50 Hz and 60 Hz mains frequency, even if there is a variation or instability in the mains frequency (see detailed description). Therefore, this selection of the modulation frequency further contributes to a noise-free, reliable measurement.

The modulation signals themselves may be sine waves, in which case the mathematical theory becomes particularly easy. However, square or rectangular waves may be used as well. Square waves are easy to generate and have another related advantage: That is, the duty cycle may be easily varied without changing the fundamental frequency, in order to adapt the signal strength in various channels. (The shape of the modulation signals should not be mixed up with the signals used for demodulation; according to the invention, the latter have always to be sinusoidal signals).

In a preferred embodiment of the invention, a low pass filter is provided through which the output signal of the multiplier circuit is fed. Likewise, it is advantageous to use a bandfilter connected between the receiver of the electromagnetic waves and the demodulator. This bandfilter blocks the harmonics, and even the fundamental frequencies of any noise, and further operates as an anti-aliasing filter for subsequent analog-to-digital conversion.

As already mentioned, one major application of the invention is pulse oximetry. In this case, the biological material examined in vivo is the patient's tissue. The electromagnetic waves are preferably waves selected from the visible and the adjoining spectra of light, in particular red and/or infrared light. The emitters of light are advantageously light-emitting diodes which are of small size and easy to incorporate into a sensor.

BRIEF DESCRIPTION OF THE DRAWINGS

Preferred embodiments of the present invention will now be explained, by means of non-limiting examples, with reference to the accompanying drawings, in which.

DESCRIPTION OF THE PREFERRED EMBODIMENTS OF THE INVENTION

FIGS. 1 through 5 illustrating the prior art approach have already been discussed above, such that there is no need to consider them further.

Figure 1:
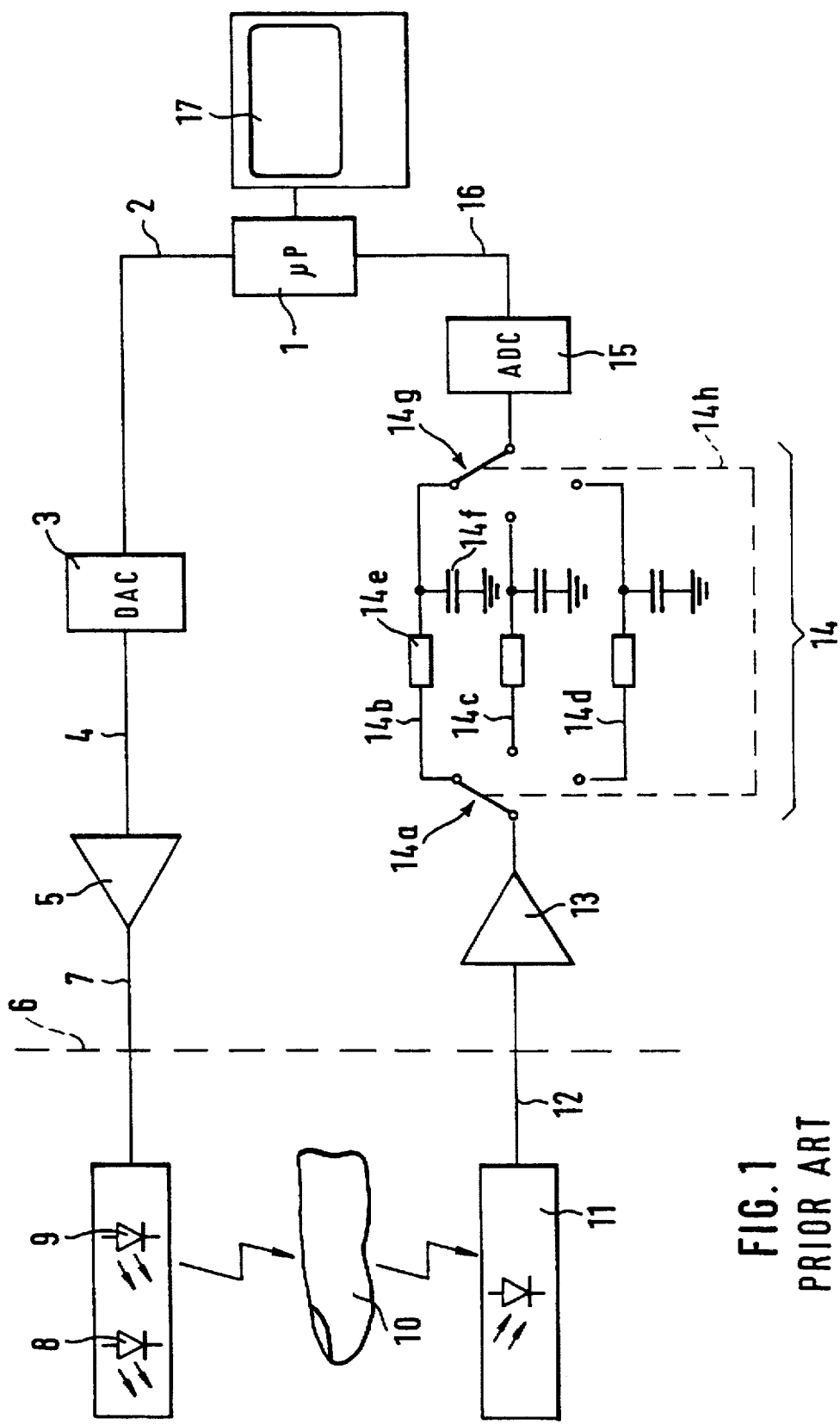
FIG. 1 depicts a block diagram of a prior art oximeter.
Figure 2:
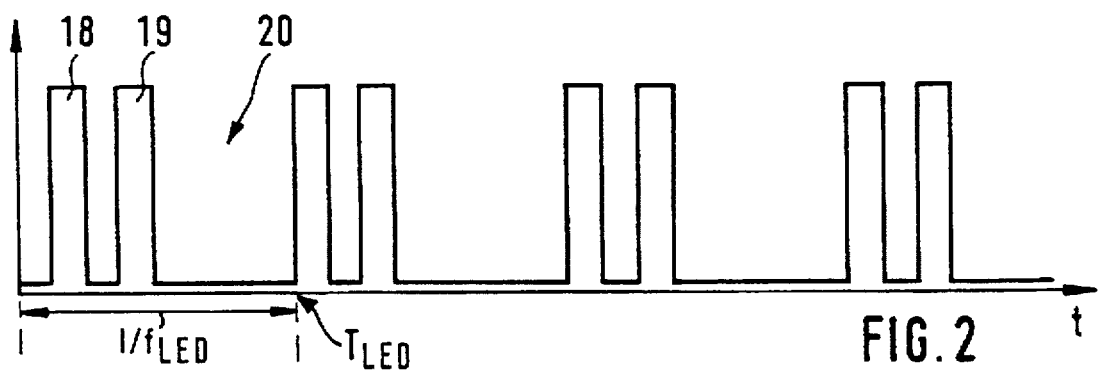
FIG. 2 is a timing diagram of the pulse train emitted by a prior art oximeter.
Figure 3A:
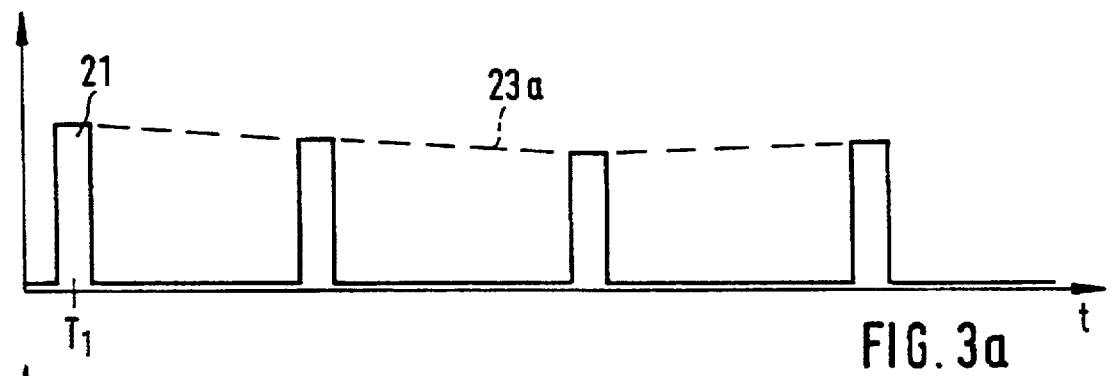
FIGS. 3a to 3c are timing diagrams of the pulse trains received by a prior art oximeter.
Figure 3B:
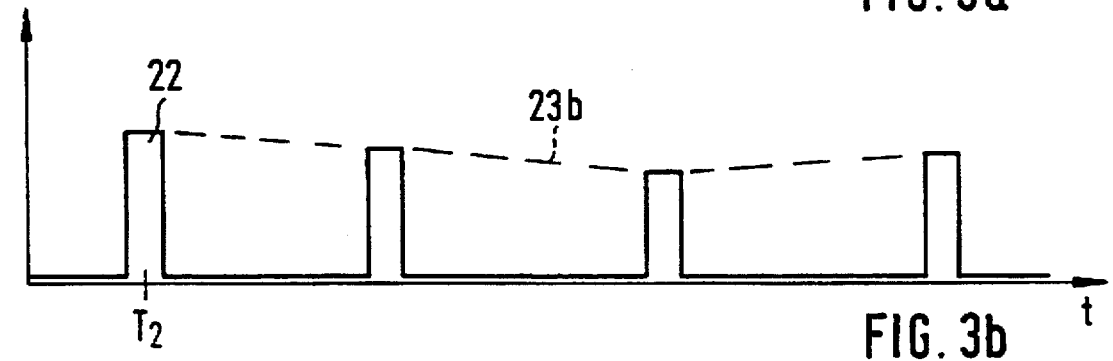
Figure 3C:
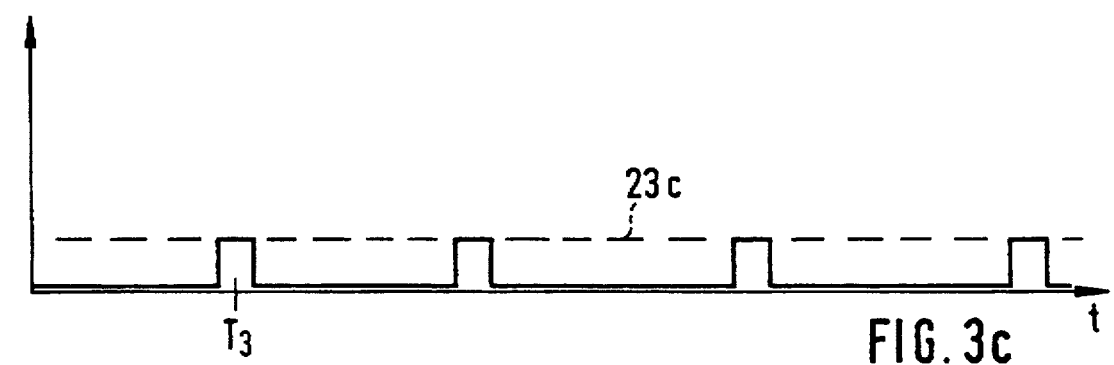
Figure 4:
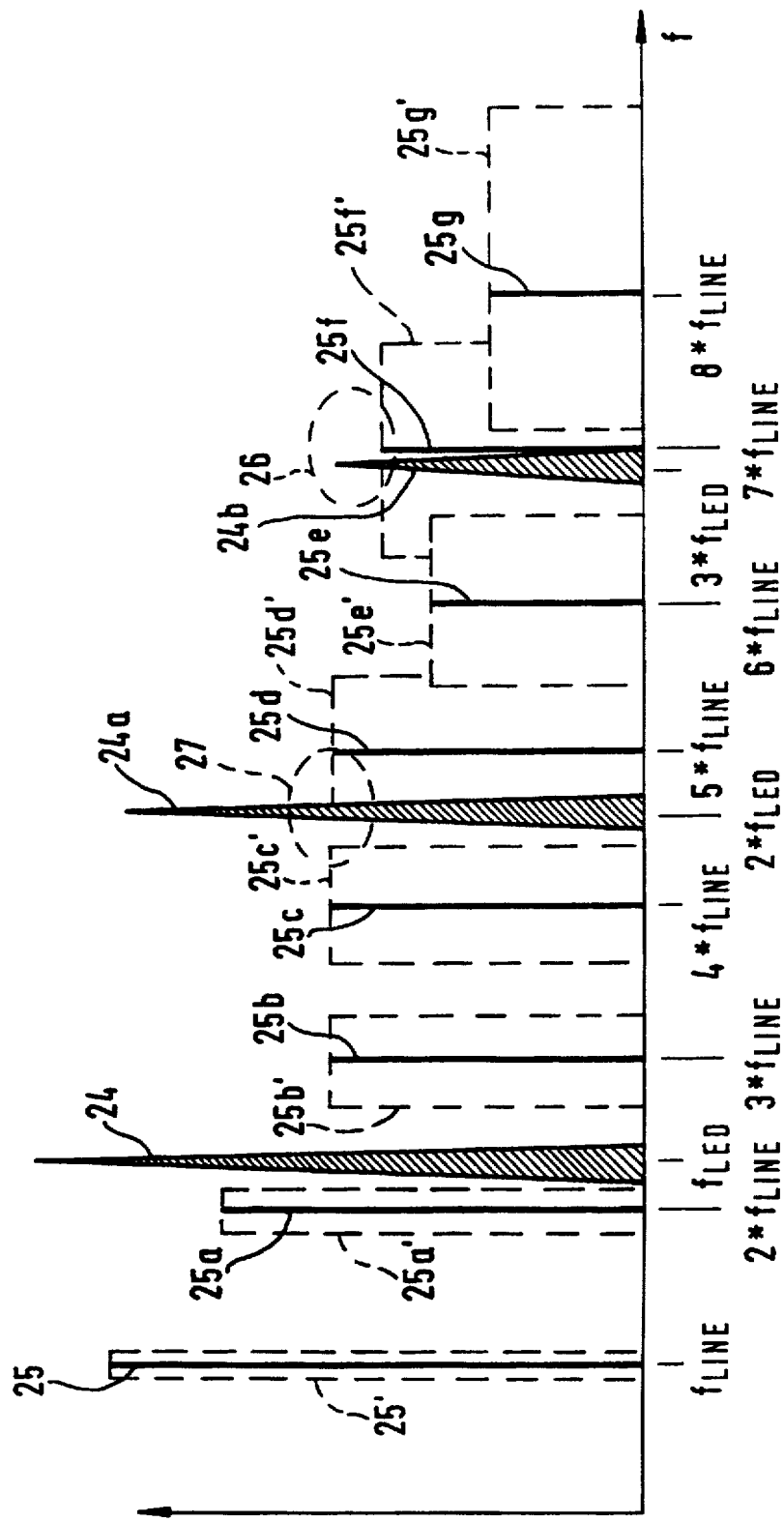
FIG. 4 is the spectrum of a prior art time multiplex oximeter prior to demodulation.
Figure 5:
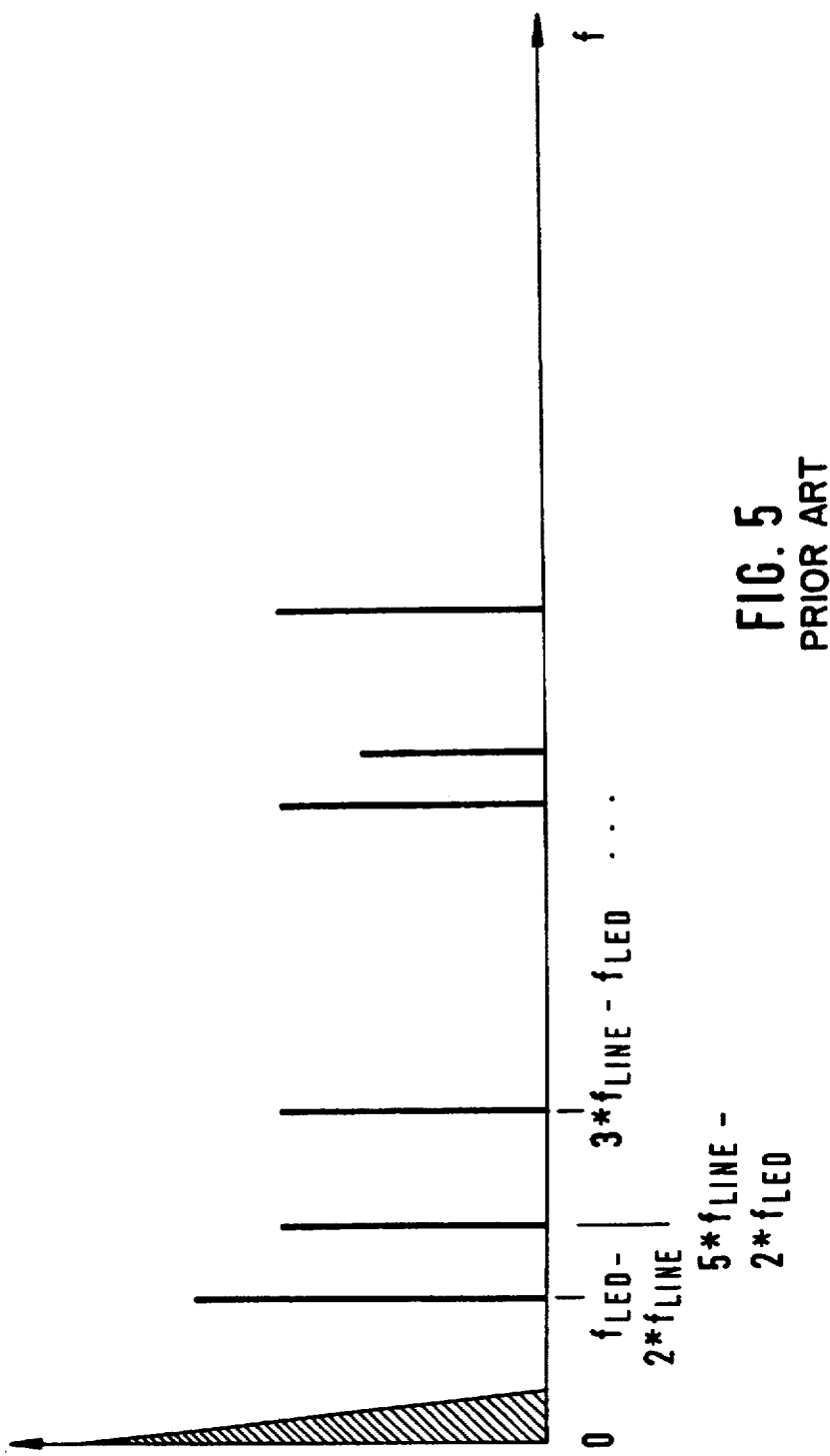
FIG. 5 depicts the effect of demodulation on the spectrum in prior art oximeters.
Figure 6:
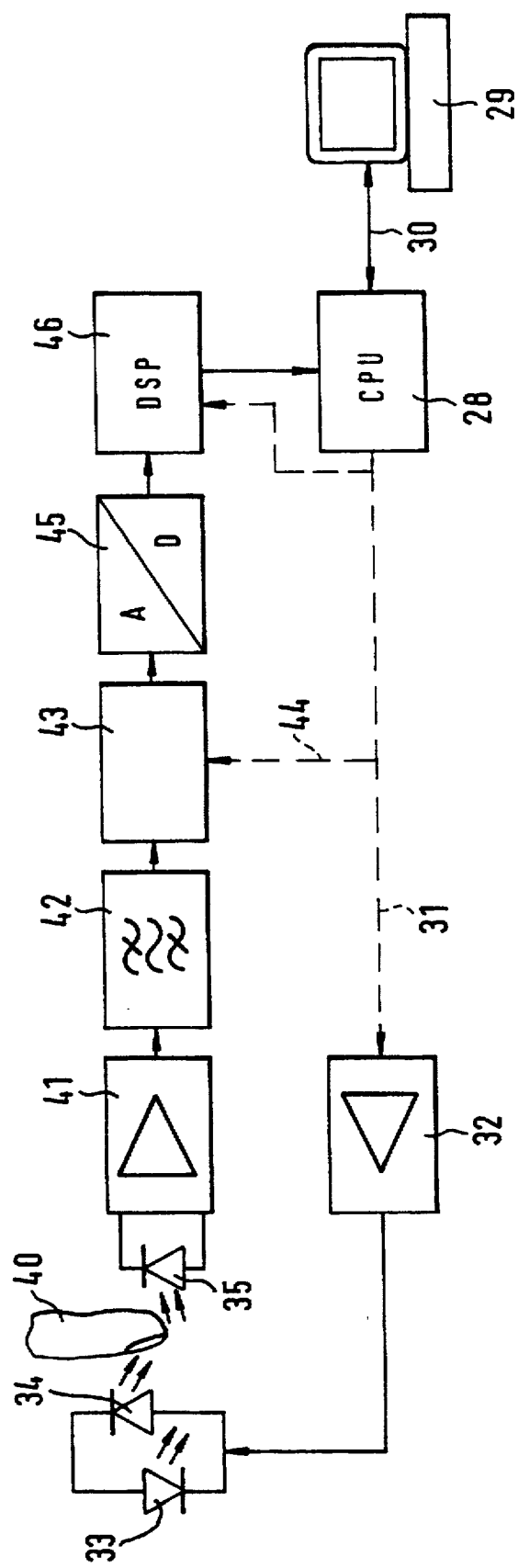
FIG. 6 is a block diagram of a pulse oximeter according to the present invention.

FIG. 6 depicts a block diagram of a two-wavelength pulse oximeter according to the invention. A microcontroller or CPU (central processing unit) 28 controls overall operation of the oximeter. In particular, it starts the measurements, adjusts the gain and controls the timing of LED excitation. Further, most of the signal processing, in particular calculation of the pulse oximetry values (oxygen saturation), of the pulse rate, the perfusion indicator and plethysmograhic waveforms is performed by CPU 28. Such algorithms—specifically suited for artifact suppression are, for example, described in another patent, U.S. Pat. No. 5,299,120, originating from the inventor of the present case. CPU 28 may further communicate with other equipment, such as a host monitor 29, via a digital link 30. The host monitor is equipped with data and waveform display capabilities, controls the alarm limits etc. It is, however, understood that the display of data, manual input etc. could also be performed locally. Further, CPU 28 may even communicate with larger systems such as hospital information systems or central stations.

The control signals for driving, i.e., for switching the LEDs are fed from CPU 28, via line 31, to an LED driver circuit 32 (the digital-to-analog converter is not shown here and may be integrated in CPU 28). LED driver circuit 32 contains current sources which operate light emitting diodes (LEDs) 33 and 34 in switched mode.

In FIG. 6, a red LED is designated as 33, and an infrared LED as 34. Both LEDs, as well as a photodiode 35, are integrated into an appropriate sensor. Such sensors are well-known in the art and need not be discussed in detail here. Reference is made, for example, to DE-C-37 03 458. The rest of the elements shown in FIG. 6 are not incorporated in the sensor, but in an appropriate monitor, a signal pick-up box or the like.

LED driver circuit 32 operates LEDs 33 and 34 in antiparallel mode. That is, red LED 33 is operated by pulses of one polarity, and infrared LED 34 is operated by pulses of the opposite polarity. This design requires less connections between the sensor and the associated monitor, although it is not a necessary prerequisite for practising the present invention.

Figure 7:
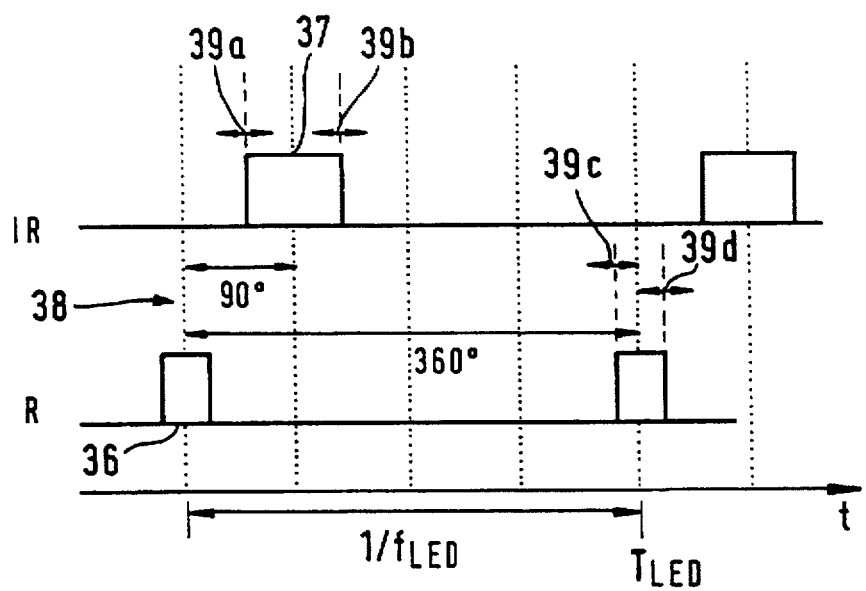
FIG. 7 depicts the shape and timing of the pulses used to control the light-emitting diodes.

The timing of the pulses generated by LED driver circuit 32 will now be discussed with reference to FIG. 7. In the shown example, these pulses are of rectangular shape, although they could also be shaped as a sine, or incorporate any other suitable shape.

The pulse driving the red LED 33 is designated as 36. Another pulse 37 (of opposite polarity, not shown in FIG. 7) drives infrared LED 34. The whole pattern restarts at $t=T_{LED}$, such that a time interval of $T_{LED}$ defines a complete cycle of 360°. An important design feature of the timing chosen in the pulse oximeter according to the invention is that the pulses of the red and the infrared LED, respectively, are offset by 90°, see reference number 38. (In terms of timing, this phase shift corresponds to $T_{LED}/4$). The reference lines for the 90° phase shift are the center of the red and infrared pulse, respectively. This is of importance if a duty cycle adjustment is necessary or desirable to balance the red and infrared signals. Such duty cycle adjustment means to adapt the pulse length of either or both of the pulses, as indicated by arrows 39a to 39d.

Returning now to FIG. 6, the light pulses generated by LEDs 33 and 34 pass human tissue, as indicated by a finger 40, and are received by photodiode 35.

The output signal of the photodiode is fed to a photo amplifier 41. This photo amplifier converts the photo current of the photodiode into a voltage. In contrast to prior art time multiplex systems, its bandwidth can be limited to $f_{FLED}$ in the present invention. Its gain is selected as high as possible, but within the limits of the maximum expected photo currents.

Reference number 42 designates a band filter. The main purpose of that stage is to block out-of-the band noise and to serve as an anti-aliasing filter for analog-to-digital sampling. The passband is designed as narrow as possible around the center frequency $f_{LED}$. The bandwidth is only slightly broader than the bandwidth of the physiological blood pulse signal. Any harmonics of the LED sampling frequency can be blocked out as they do not contribute to the demodulated signal.

Programmable gain amplifier 43 (controlled by CPU 28, see line 44) ensures that the filtered signal fits within the input range of analog-to-digital converter (ADC) 45. It is therefore used to adapt to the large dynamic variability of the photoelectrical signal. As pulse oximetry sensors are used on very different body locations, the different tissue types and thickness between emitters and receivers result in largely different light intensities. The gain of that amplifier is controlled by the CPU to adapt the output amplitude to fit the full scale input range of the analog-to-digital converter for good quantization.

Digital signal processor (DSP) 46 represents, to some extent, the "heart" of the present invention. It demodulates the received, filtered and digitized pulses with sinusoidal functions. In the shown embodiment, this demodulation is performed in the digital domain—i.e., by a digital processor—, and in fact the functionality of DSP 46 may be provided by CPU 28 as well. However, this is not a necessary requirement; DSP 46 may also be a separate signal processor in digital or analog technology. The major functions of DSP 46 are demodulation, low pass filtering and down sampling.

Figure 8:
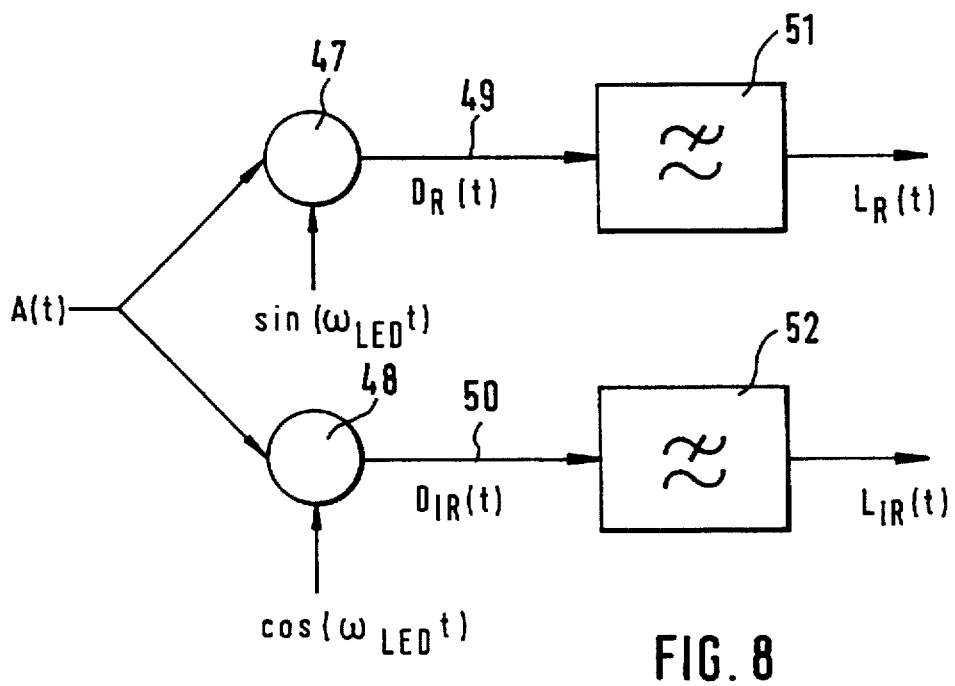
FIG. 8 is a block diagram of the digital signal processor.

In order to explain the functionality provided by DSP 46, reference is now made to FIG. 8. The output signal of ADC 45, A(t), is fed to two multipliers 47 and 48, which perform a multiplication with sinusoidal functions $\sin(\omega_{LED}t)$ and $\cos(\omega_{LED}t)$, respecitvely. The skilled man will immediately note that the use of sine and cosine functions corresponds to a phase shift of 90°, just because $\sin(90°+\alpha)=\cos(\alpha)$. The demodulated signals are now fed, via lines 49 and 50, to respective digital low pass filters 51 and 52. Their functionality will be discussed in greater detail below.

For the following discussion of the mathematical theory, it will be assumed that the LEDs are driven so that the optical emissions of the LEDs are pure sine waves, shifted by 90° in phase, e.g. the red LED with a sine and the infrared LED with a cosine. In the actual embodiment, this is not the case, as shown above; however, the mathematical background may be explained more easily by the assumption of sinusoidal driving.

The output of ADC 45, i.e., the input signal to DSP 46 is then $$A(t) = A_R(t) + A_{IR}(t) \tag{2}$$

with $$A_R(t) = A_R * \sin(2\pi * f_{LED} * t + \phi) \tag{3a}$$

$$A_{IR}(t) = A_{IR} * \cos(2\pi * f_{LED} * t + \phi) \tag{3b}$$

wherein $\phi$ is the phase shift between the optical LED signal and the digitized photo receiver signal at the ADC output, herein also referred to as system phase shift, and $\omega_{LED} = 2\pi * f_{LED}$.

$A_R$ and $A_{IR}$ themselves are modulated by the patient's blood pulse:

$$A_R = S_R(t) \tag{4a}$$

$$A_{IR} = S_{IR}(t) \tag{4b}$$

wherein $S_R(t)$ and $S_{IR}(t)$ are composed of a DC and an AC component. (The DC component represents the constant tissue absorption, whereas the AC component is related to the variable absorbance due to pulsatile blood volume change).

Demodulation as multiplication with sine waves reveals then at the outputs of multipliers 47 and 48:

$$D_R(t) = A(t) * M_R(t) \tag{5a}$$

$$D_{IR}(t) = A(t) * M_{IR}(t) \tag{5b}$$

with $$M_R(t) = \sin(\omega_{LED} * t + \sigma) \tag{5c}$$

and $$D_{IR}(t) = \cos(\omega_{LED} * t + \sigma) \tag{5d}$$

As will be explained below in more detail, the CPU is programmed to determine the system phase shift $\phi$ in order to make the demodulator phase shift $\sigma$ equal to the system phase shift $\phi$.

Given that the demodulator phase a is made equal to the system phase shift $\phi$ ($\sigma = \phi$) and solving the equation results in the following fractions:

$$D_R(t) = \tfrac{1}{2}A_R - \tfrac{1}{2}A_R * \cos(2\omega_{LED} * t + 2\phi) + \tfrac{1}{2}A_{IR} * \sin(2\omega_{LED} * t + 2\phi) \tag{6a}$$

$$D_{IR}(t) = \tfrac{1}{2}A_{IR} - \tfrac{1}{2}A_{IR} * \cos(2\omega_{LED} * t + 2\phi) + \tfrac{1}{2}A_R * \sin(2\omega_{LED} * t + 2\phi) \tag{6b}$$

So far, the demodulated signals contain both the sum and difference frequencies. These signals are then fed through digital low pass filters 51 and 52 which have a cut-off frequency just beyond the physiological bandwidth of the blood pulse. In an ideal low pass filter, this operation cuts off all harmonics of the modulation frequency $f_{LED}$.

In this case, the output of low-pass filters 51 and 52 is $$L_R(t) = \tfrac{1}{2}A_R \tag{7a}$$

$$L_{IR}(t) = \tfrac{1}{2}A_{IR} \tag{7b}$$

These signals correspond ideally to the optical absorption of the red and infrared signals at the photodiode. Note that signals $A_R$ and $A_{IR}$ are not constant, but are modulated by the blood pulsation itself.

Signals $L_R(t)$ and $L_{IR}(t)$ are now small-band signals, which means that the data rate is reduced to a level desirable by standard down-sampling techniques. It is further understood that all other frequencies in the received signal, like electrical or optical interference, are blocked completely by the method according to the present invention. The result is very pure, noise-free signal reconstruction. Therefore fore, it is possible to choose an interference-free modulation band, even at lowest frequencies. In the preferred embodiment of the present invention, the LED modulation frequency is selected as $f_{LED} = 275$ Hertz.

Figure 9:
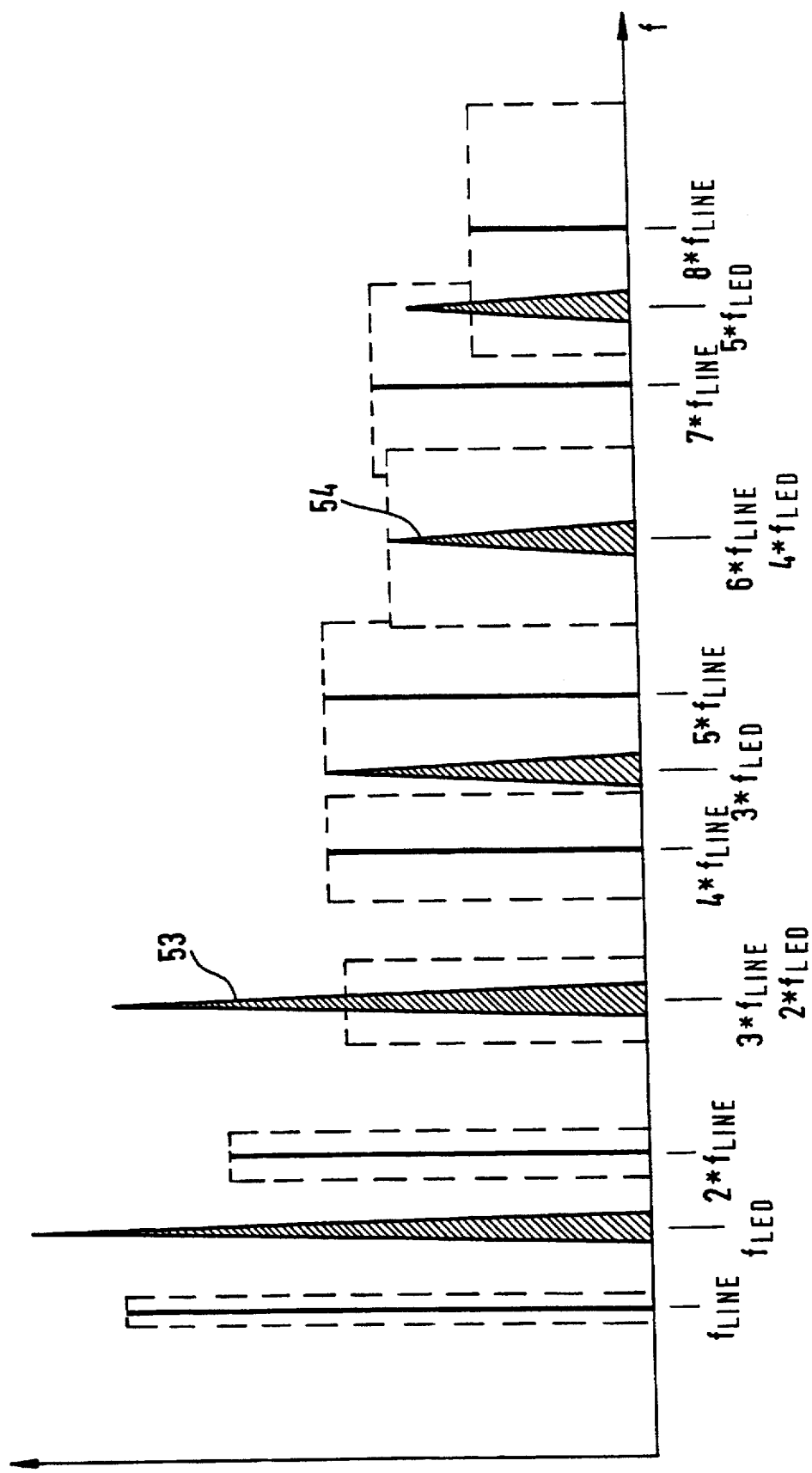
FIG. 9 is an example of a spectrum processed by an apparatus according to the present invention.

In order to explain the advantages of the present invention, as compared to the prior art time multiplex approach, and in particular the advantages of demodulation with sine waves, preferably with a phase offset of 90°, reference is now made to FIG. 9. This figures depicts a typical spectrum in a representation similar to FIG. 4. However, FIG. 9 depicts even a more sensitive case, just because some of the harmonics of the LED modulation frequency, and some harmonics of the mains frequency coincide. Reference numbers 53 and 54 relate to such cases:

$$2 * f_{LED} = 3 * f_{Line} \text{(Ref. no. 53)} \tag{8a}$$

$$4 * f_{LED} = 6 * f_{Line} \text{(Ref. no. 54)} \tag{8b}$$

Figure 10:
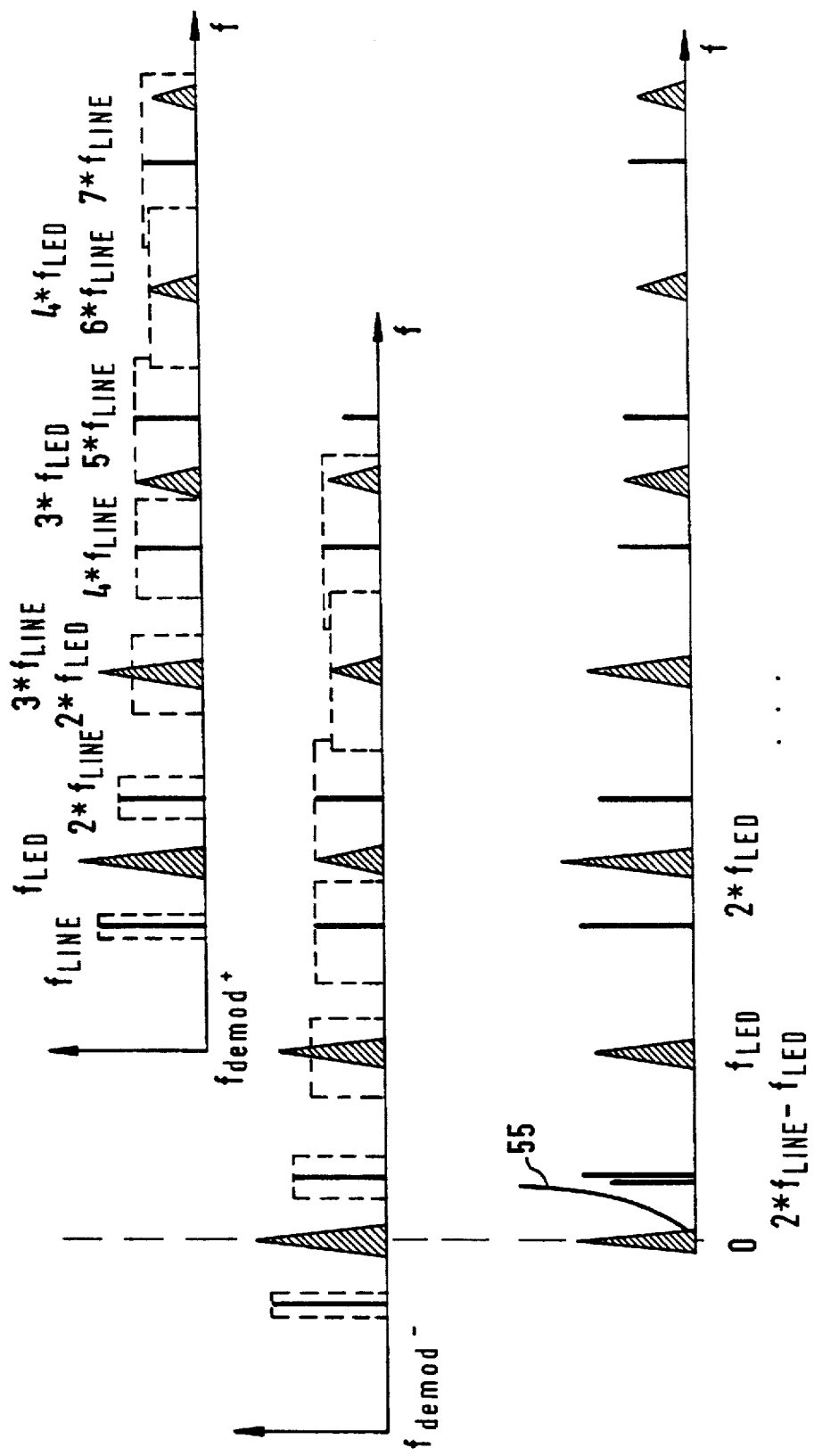
FIG. 10 shows the effect of the quadrature modulation technique according to the present invention on the signal-to-noise improvements.

The demodulation technique according to the present invention is, however, still able to filter the harmonics of the mains frequency out, as will now be shown by means of FIG. 10.

The quadrature demodulation technique according to the present invention, in combination with sampling, produces a shift of the related spectra, together with the generation of sum and difference frequencies. The amount of frequency shift is $f_{demod}$, i.e., the frequency of the sine functions used for demodulation, which is in this case identical to the LED modulation frequency $f_{LED}$. The shifted spectra (two in total) are shown in FIG. 10, namely the spectrum shifted by $+f_{demod}$ (upper diagram) and the spectrum shifted by $-f_{demod}$ (second diagram from top). (The frequency designations are, except of the shift, identical in both diagrams, so they are only shown in the upper one).

The resulting spectrum is shown in the lower diagram. A low pass filters out the base band and blocks all higher frequencies (its attenuation characteristics is designated by reference number 55). As can be easily observed, the baseband signal does not contain any noise resulting from the harmonics of the power line or other sources of interference, which makes up the great advantage of the present invention over the prior art approach.

What follows is a detailed description of preferred embodiments of the present invention which are useful to eliminate the influence of the system phase shift $\phi$ out of the result of the analysis.

In accordance with the first embodiment, the system phase shift $\phi$ of the system, shown for example in FIG. 6, is determined, and on the basis of the determined system phase shift $\phi$ the phase shift $\sigma$ of the sinusoidal demodulation signals with respect to the first and second modulation signals is adjusted.

An important function is the capability to measure the phase shift $\phi$ of the system. This phase shift $\phi$ is defined as the phase difference between the excitation signals which drive each LED and the receiving signal as sampled by the A/D converter.

A software routine in the CPU performs that measurement routinely at power up and selected events during normal operation. Events can be programmed time intervals, a change of the sensor connected, changing the gain of programmable gain amplifier, and thereby its filter characteristics, and so on.

Subsequently, a particular embodiment of a procedure for determining the system phase shift φ is described.

Firstly, the normal operating mode is interrupted. The red LED is disabled, whereas the infrared LED is driven in its normal mode. Then, in the preferred embodiment, a default phase σ equal $\sigma_{DEF}$ is applied to the demodulator. After a waiting time of some milliseconds, until the low pass filters have settled, the real-time values in the red channel $L_R'$ and the infrared channel $L_{IR}'$ are stored. On the basis of this stored real-time values the correct phase shift σ to be applied to the demodulator is calculated, see the following equation. Afterwards, the correct phase shift σ is applied to the demodulator.

Subsequently, the red LED is enabled again. After having awaited until low pass filters have settled again, the normal operating mode is resumed.

The calculation of the correct phase shift σ is done by the following equation:

$$\epsilon = \arctan\left(\frac{L'_R}{L'_{IR}}\right)$$

Figure 11:
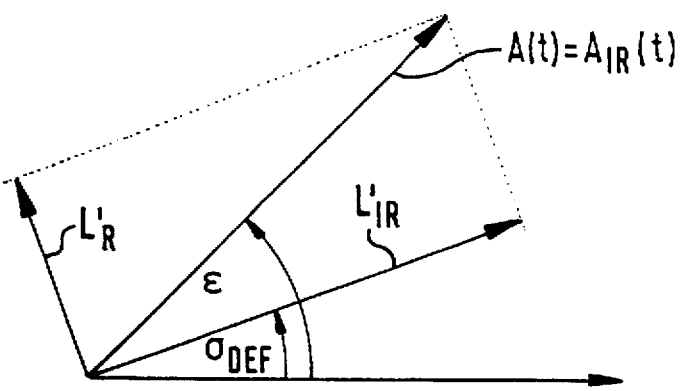
FIG. 11 and FIG. 12 are vector diagrams for illustrating phase shift measurements.

The vector diagram shown in FIG. 11 shows the situation during the phase measurement. The arrow designated by $L'_R$ represents the red demodulation vector.

The arrow designated by $L'_{IR}$ represents the infrared demodulation vector. The arrow arranged between these arrows represents the received electromagnetic wave A(t). It is: $A(t)=A_{IR}(t)$ since $A_R(t)=0$ during phase measurement. This phase adjust vector diagram represents the situation prior to adjustment.

The value of the demodulated signal in the red channel would be close to 0, if the default phase ($\sigma_{DEF}$) was already correct. In general, a cross-talk $L_R'$ from the infrared exitation exists because the default phase (or the phase from a prior adjustment) is only close to the correct value, that means the correction angle ε≠0.

Figure 12:
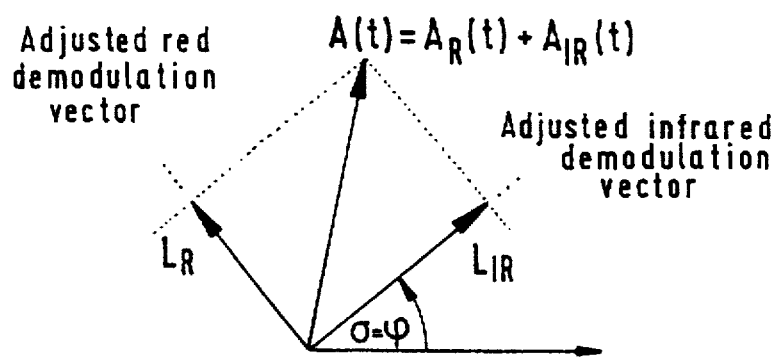

The vector diagram shown in FIG. 12 shows the situation after having applied the phase adjustment. The arrow on the left hand side $L_R$ represents the adjusted red demodulation vector. The arrow on the right hand side $L_{IR}$ represents the adjusted infrared demodulation vector. The middle arrow represents the received electromagnetic waves A(t) being a combination of the electromagnetic wave $A_R(t)$ (red excitation) and the electromagnetic wave $A_{IR}(t)$ (infrared excitation). As can be seen from FIG. 12, the correct phase shift σ to be applied to the demodulator corresponds to the system phase shift φ.

The advantage of this auto-phase-adjust is that it compensates for any phase shifts and drifts which can occur for reason of temperature, aging and component tolerances. It also adapts to changing sensor characteristics. A further advantage of this implementation of automatic adjust is that it can be applied without interruption of the continuous plethysmographic wave form, if the pleth signal is derived from the infrared LED.

It is understood that the role of red and infrared could be exchanged without changing the fundamental idea.

Another advantage of adjusting the demodulation phase to match the system phase, σ=φ, is that the demodulated and filtered signal $L_R$ and $L_{IR}$ are only positive. This avoids restricting the numeric range by a factor of two in order to allow for signed integer values.

What follows is a preferred embodiment of a further method to compensate for the system phase shift φ in accordance with the present invention. The method described below determines the system phase too as explained above, but does not apply a compensation afterwards. It rather uses the determined or measured phase φ in a correction calculation.

In the beginning, the demodulator is running with any fixed phase. In the example below it is set to $\sigma=\sigma_{DEF}=0$ for simplification of the equations.

Using equations (1) to (5d) yields:

$$D_R(t)=\tfrac{1}{2}A_R[\cos(\phi)-\cos(2\omega_{LED}*t+\sigma)]+\tfrac{1}{2}A_{IR}[\sin(-\phi)*\sin(2\omega_{LED}*t+\sigma)] \quad (14a)$$

$$D_{IR}(t)=\tfrac{1}{2}A_R[\sin(\phi)+\sin(2\omega_{LED}*t+\sigma)]+\tfrac{1}{2}A_{IR}[\cos(\phi)*\cos(2\omega_{LED}*t+\sigma)] \quad (15a)$$

Setting σ=0 yields:

$$D_R(t)=\tfrac{1}{2}A_R[\cos(\phi)-\cos(2\omega_{LED}*t)]+\tfrac{1}{2}A_{IR}[\sin(-\phi)*\sin(2\omega_{LED}*t)] \quad (14b)$$

$$D_{IR}(t)=\tfrac{1}{2}A_R[\sin(\phi)+\sin(2\omega_{LED}*t)]+\tfrac{1}{2}A_{IR}[\cos(\phi)*\cos(2\omega_{LED}*t)] \quad (15b)$$

After low-pass filtering the output signals are:

$$L_R(t)=\tfrac{1}{2}A_R*\cos(\phi)+\tfrac{1}{2}A_{IR}*\sin(-\phi) \quad (16)$$

$$L_{IR}(t)=\tfrac{1}{2}A_R*\sin(\phi)+\tfrac{1}{2}A_{IR}*\cos(\phi) \quad (17)$$

On the basis of equation (16) and equation (17) a matrix can be defined:

$$[C] = \begin{bmatrix} \cos\phi & -\sin\phi \\ \sin\phi & \cos\phi \end{bmatrix} \quad (18)$$

The electromagnetic waves received by photodiode 35 can be written as an input vector:

$$[A] = \begin{bmatrix} A_R \\ A_{IR} \end{bmatrix} \quad (19)$$

After the demodulation by DSP 46 an output vector can be defined:

$$[L] = \begin{bmatrix} L_R \\ L_{IR} \end{bmatrix} \quad (20)$$

On the basis of the matrix [C], the input vector [A], and the output vector [L], the original signals ($A_R$ and $A_{IR}$) can be recovered continuously by computing the matrix correction:

$$[A]=[C]^{-1}\cdot[L] \quad (12)$$

$[C]^{-1}$ is the inverse matrix of [C].

The phase measurement procedure is described below.

Firstly, the normal operating mode is interrupted, the red LED is disabled and the infrared LED is continuously driven in normal mode. After waiting for some milliseconds until the low-pass filters have settled, real-time values in the "red" channel $L_R'$ and the "infrared" channel $L_{IR}'$ are stored. Subsequently, the system phase shift φ is calculated on the basis of equation (13). The red LED is enabled again, and after a waiting time, until low-pass filters have settled, the normal operating mode is resumed.

The normal operating mode in this case means applying equation (21) with the previously determined phase shift φ. The correction calculation described above can be performed for example by the CPU 28.

Another method to overcome signal cross-coupling between "red" and "infrared" channels in accordance with the present invention is to use an all-pass filter anywhere in the signal path between photoreceiver and demodulator. The all-pass filter has the function of a phase shifter. This all-pass filter should have a phase shift δ at the excitation base frequency $f_{LED}$ which yields to:

$$\delta + \phi = n * 360° \quad (22)$$

with n=1,2,...

Such a filter would be ideally realized in the digital domain with programmable filter constants. The phase characteristics of such a all-pass filter in the digital domain can be adjusted according to a measured or determined system phase shift. In this case, the phase measurement procedure would be as follows.

In the beginning, the normal operating mode is interrupted, the red LED is disabled, the infrared LED is continuously driven, and the all-pass function is switched off (by-pass etc.). Thereafter, there is a waiting time for some milliseconds until the low-pass filters have settled. After this waiting time, the real-time values in the "red" channel $L_R$ and the "infrared" channel $L_{IR}'$, are stored. On the basis of these stored values and equation (13) the system phase shift φ is calculated.

Subsequently, the phase shift δ which the all-pass filter should have is determined according equation (22). On the basis of this determined phase shift filter, the appropriate filter constants for this type of all-pass filter are selected. After having enabled the red LED again and having waited, until low-pass filters have settled, the normal operating mode is resumed. The normal operating mode in this case means activating the all-pass function in the signal flow with the determined characteristics in order to produce a phase shift δ of the received electromagnetic waves in the signal path between photoreceiver and modulator.

Besides the method to measure the phase of the incoming signal relative to the transmitted electromagnetic waves as described above there exist other methods to measure this phase. A common step is always to change at least one of the LED's intensity by a known amount. The procedure explained above is a special case where the red LED's intensity is set to 0. This gives a best measurement resolution and makes calculation easier.

However, it is understood that any known change of one or a combination of the two LED's intensities could be used to determine the phase. An advantage of switching the intensity only to a reduced level, like 0.5, would be the possibility to continue with a normal SpO₂ measurement without interruption.

Figure 13:
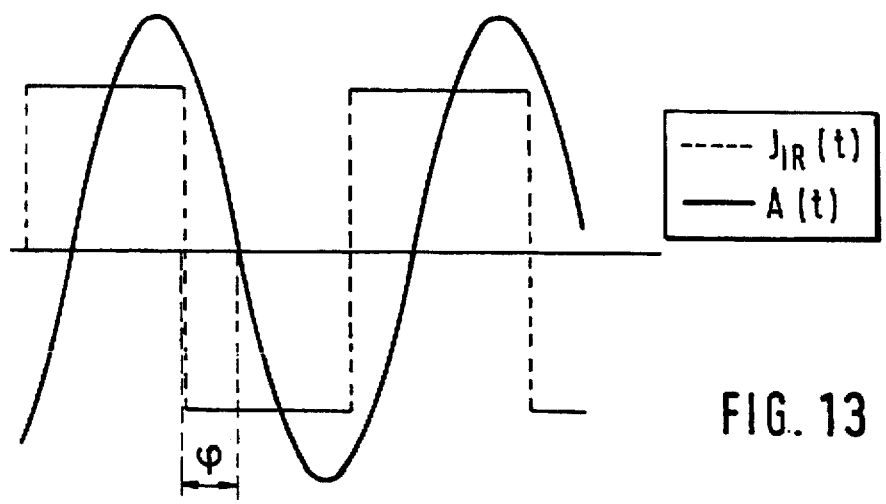
FIG. 13 is a schematic representation for illustrating direct phase measurement on an unfiltered signal.

Referring to FIG. 13, a further method to determine the system phase shift φ is described. In this measurement, the difference in the zero-crossing between the incoming signal A(t) and the LED drive signal $J_R(t)$ and $J_{IR}(t)$ is measured before demodulation, rather than measuring the amplitudes of the incoming signals on the low-pass filtered side. In FIG. 13, the incoming signal A(t) is shown as a sinusoidal wave form. The "infrared" excitation wave is shown as a quare waveform $J_{IR}(t)$. As can be seen from FIG. 13, the phase difference φ of this two waveforms which corresponds to the system phase shift φ is determined on the basis of a negative zero-crossing of both these signals. The phase shift determined by this method can be used in the same way as the phase shift determined on the basis of equation (13).

It will be appreciated by those skilled in the art that the principle of sinusoidal demodulation as disclosed herein is also applicable to multi-wavelength oximetry. If a third and forth LED is used, a further LED modulation frequency has to be selected. In general, for n LEDs, n/2 modulation frequencies have to be used, just because each frequency channel can contain 2 independent information data in quadrature mode. The only condition for these different modulation frequencies is that they are offset by more than the physiological bandwidth of the blood pulse.

It is also clear that the sinusoidal demodulation can be applied in a two LED pulse oximeter without the quadrature concept, but with only the sinusoidal demodulation, if there is a different modulation frequency chosen for each LED.

The great advantage of interference immunity of this system may also be applied to other sensoric measurements where ambient noise is an issue, not only in medical instrumentation. It is always possible where an excitation is used for stimulation. Examples are impedance measurements in bridges like pressure strain gauges or spectrometer devices with chopped sources.

What is claimed is:

1. Method for measuring medical parameters of a patient by irradiation of electromagnetic waves into a sample and for measurement and subsequent analysis of the electromagnetic waves which have passed through said sample, said method comprising the steps of:

(1.1) generating first and second modulation signals having equal frequencies and having a first phase difference of substantially 90°;

(1.2) irradiating a first electromagnetic wave of a first wavelength into said sample under control of said first modulation signal;

(1.3) irradiating a second electromagnetic wave of a second wavelength different from the first one into said sample under control of said second modulation signal;

(1.4) receiving electromagnetic waves of both wavelengths which have passed through said sample;

(1.5) demodulating signals representative of the received electromagnetic waves by multiplying the same with a first sinusoidal demodulation signal and with a second sinusoidal demodulation signal having the first phase difference with respect to said first sinusoidal signal, said first and second sinusoidal demodulation signals having an identical frequency as said first and second modulation signals, such as to generate a first and a second demodulated signal;

wherein the first and the second sinusoidal demodulation signals have a phase difference relative to the first and second modulation signals corresponding to a system phase shift; and (1.6) analyzing said demodulated signals.

2. Method according to claim 1, comprising the step of determining said system phase shift and the step of adjusting said phase shift of the first and second sinusoidal signals relative to the first and second modulation signals in accordance with said determined system phase shift.

3. Method according to claim 2, wherein said determining said system phase shift includes the steps of:

reducing an amplitude of one of the first and second electromagnetic waves;

measuring of amplitudes of the first and second demodulated signals; and determining the system phase shift on the basis of the measured amplitudes of the first and the second demodulated signal.

4. Method according to claim 2, wherein said determining said system phase shift includes the steps of:

reducing an amplitude of one of the first and second electromagnetic waves; and determining the difference in a zero-crossing between the received electromagnetic waves and the other of the first and second electromagnetic waves.

5. Method according to claim 1, wherein the frequency of said first and second modulation signals is basically f=275 Hertz.

6. Method according to claim 1, wherein said first and second modulation signals are square-wave signals.

7. Method according to claim 1, wherein said first and second modulation signals are sinusoidal signals.

8. Method according to claim 1 comprising the step of low-pass filtering the demodulated signals.

9. Method according to claim 1 comprising the step of band-pass filtering the received electromagnetic waves before the demodulation step.

10. Method according to claim 1, wherein said electromagnetic waves are waves selected from the visible and/or the adjoining spectra of light.

11. Method according to claim 1, wherein said medical parameter is oxygen saturation.

12. Method according to claim 1, wherein said electromagnetic waves are waves selected from red or infra-red light.

13. Method for measuring medical parameters of a patient by irradiation of electromagnetic waves into a sample and for measurement and subsequent analysis of the electromagnetic waves which have passed through said sample, said method comprising the steps of:
  (12.1) generating first and second modulation signals having equal frequencies and having a first phase difference of substantially 90°;
  (12.2) irradiating a first electromagnetic wave of a first wavelength into said sample under control of said first modulation signal;
  (12.3) irradiating a second electromagnetic wave of a second wavelength different from the first one into said sample under control of said second modulation signal;
  (12.4) receiving electromagnetic waves of both wavelengths which have passed through said sample;
  (12.5) demodulating signals representative of the received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal;
  (12.6) analyzing said demodulated signals taking into account a system phase shift.

14. Method according to claim 13, wherein said analysing step comprises the steps of:
  determining said system phase shift; and
  correcting said demodulated signals on the basis of said determined system phase shift.

15. Method according to claim 14, wherein said determining said system phase shift includes the steps of:
  reducing an amplitude of one of the first and second electromagnetic waves;
  measuring of amplitudes of the first and second demodulated signals; and
  determining the system phase shift on the basis of the measured amplitudes of the first and the second demodulated signal.

16. Method according to claim 15, wherein the reducing of the amplitude of one of the first and second electromagnetic waves comprises turning off the amplitude of this electromagnetic wave.

17. Method according to claim 14, wherein said determining said system phase shift includes the steps of:
  reducing an amplitude of one of the first and second electromagnetic waves; and
  determining a difference in a zero-crossing between the received electromagnetic waves and the other of the first and second electromagnetic waves.

18. Method according to claim 13, wherein said analysing step comprises the steps of:
  determining the system phase shift;
  calculating a matrix [C] based on the system phase shift according to $$[C] = \begin{bmatrix} \cos\phi & -\sin\phi \\ \sin\phi & \cos\phi \end{bmatrix};$$

calculating an inverse matrix $[C]^{-1}$ based on the matrix [C];
  determining an output vector $$[L] = \begin{bmatrix} L_R \\ L_{IR} \end{bmatrix}$$

based on the amplitudes $L_R$, $L_{IR}$ of the demodulated signals; and
  calculating a corrected output vector $[A]=[C]^{-1}\cdot[L]$.

19. Method according to claim 13, wherein the frequency of said first and second modulation signals is basically f=275 Hertz.

20. Method according to claim 13, wherein said first and second modulation signals are square-wave signals.

21. Method according to claim 13, wherein said first and second modulation signals are sinusoidal signals.

22. Method according to claim 13, comprising the step of low-pass filtering the demodulated signals.

23. Method according to claim 13 comprising the step of band-pass filtering the received electromagnetic waves before the demodulation step.

24. Method according to claim 13, wherein said electromagnetic waves are waves selected from the visible and/or the adjoining spectra of light.

25. Method according to claim 13, wherein said medical parameter is oxygen saturation.

26. Method according to claim 13, wherein said electromagnetic waves are waves selected from red or infra-red light.

27. Method for measuring medical parameters of a patient by irradiation of electromagnetic waves into a sample and for measurement and subsequent analysis of the electromagnetic waves which have passed through said sample, said method comprising the steps of:
  (25.1) generating first and second modulation signals having equal frequencies and having a first phase difference of substantially 90°;
  (25.2) irradiating a first electromagnetic wave of a first wavelength into said sample under control of said first modulation signal;
  (25.3) irradiating a second electromagnetic wave of a second wavelength different from the first one into said sample under control of said second modulation signal;
  (25.4) receiving electromagnetic waves of both wavelengths which have passed through said sample;

(25.5) generating delayed received electromagnetic waves by adding a phase shift to the received electromagnetic waves which yields, together with a system phase shift, a total phase shift of the received electromagnetic waves relative to the first and second electromagnetic waves of substantially an integral multiple of 360°;

(25.6) demodulating signals representative of the delayed received electromagnetic waves by multiplying the same with a first sinusoidal demodulation signal and with a second sinusoidal demodulation signal having the first phase difference with respect to said first sinusoidal signal, said first and second sinusoidal demodulation signals having an identical frequency as said first and second modulation signals, such as to generate a first and a second demodulated signal; and (25.7) analyzing said demodulated signals.

28. Method according to claim 27, wherein said phase shift is added to the received electromagnetic waves by a digital all pass filter comprising programmable filter constants.

29. Method according to claim 27, wherein said phase shift is adjusted in accordance with the steps of:
reducing an amplitude of one of the first and second electromagnetic waves;
measuring of amplitudes of the first and second demodulated signals;
determining the system phase shift on the basis of the measured amplitudes of the first and second demodulated signals; and
adjusting the phase shift to yield together with the system phase shift a phase shift of an integral multiple of 360°.

30. Method according to claim 29, wherein the reducing of the amplitude of one of the first and second electromagnetic waves comprises turning off the amplitude of this electromagnetic wave.

31. Method according to claim 27, wherein the frequency of said first and second modulation signals is basically f=275 Hertz.

32. Method according to claim 27, wherein said first and second modulation signals are square-wave signals.

33. Method according to claim 27, wherein said first and second modulation signals are sinusoidal signals.

34. Method according to claim 27 comprising the step of low-pass filtering the demodulated signals.

35. Method according to claim 27, wherein said electromagnetic waves are waves selected from the visible and/or the adjoining spectra of light.

36. Method according to claim 27, wherein said medical parameter is oxygen saturation.

37. Method according to claim 36 comprising the step of band-pass filtering the received electromagnetic waves before the demodulation step.

38. Method according to claim 27, wherein said electromagnetic waves are waves selected from red or infra-red light.

39. Apparatus for measuring medical parameters of a patient by irradiation of electromagnetic waves into a sample and for measurement and subsequent analysis of the electromagnetic waves which have passed through said sample, said apparatus comprising:
means for generating first and second modulation signals having equal frequencies and having a first phase difference of substantially 90°;
means for irradiating a first electromagnetic wave of a first wavelength into said sample under control of said first modulation signal;
means for irradiating a second electromagnetic wave of a second wavelength different from the first one into said sample under control of said second modulation signal;
means for receiving electromagnetic waves of both wavelengths which have passed through said sample;
means for demodulating signals representative of the received electromagnetic waves by multiplying the same with a first sinusoidal demodulation signal and with a second sinusoidal demodulation signal having the first phase difference with respect to said first sinusoidal signal, said first and second sinusoidal demodulation signals having the same frequency as said first and second modulation signals, such as to generate a first and a second demodulated signal;
wherein the first and the second sinusoidal demodulation signals have a phase difference relative to the first and second modulation signals corresponding to a system phase shift; and
means for analyzing said demodulated signals.

40. Apparatus according to claim 39, comprising further a means for determining said system phase shift and for adjusting said phase shift of the first and second sinusoidal signals relative to the first and second modulation signals in accordance with said determined system phase shift.

41. Apparatus according to claim 39, wherein the frequency of said first and second modulation signals is basically f=275 Hertz.

42. Apparatus according to claim 39, wherein said first and second modulation signals are square-wave signals.

43. Apparatus according to claim 39, wherein said first and second modulation signals are sinusoidal signals.

44. Apparatus according to claim 39 comprising a low pass filter through which the demodulated signals are fed.

45. Apparatus according to claim 39 comprising a band-filter connected between said means for receiving electromagnetic waves and said demodulating means.

46. Apparatus according to claim 39, wherein said electromagnetic waves are waves selected from the visible and/or the adjoining spectra of light.

47. Apparatus according to claim 39, wherein said apparatus is a pulse oximeter, and said medical parameter is oxygen saturation.

48. Apparatus according to claim 39, wherein said irradiating means are light-emitting diodes.

49. Method according to claim 39, wherein said electromagnetic waves are waves selected from red or infra-red light.

50. Apparatus for measuring medical parameters of a patient by irradiation of electromagnetic waves into a sample and for measurement and subsequent analysis of the electromagnetic waves which have passed through said sample, said method comprising the steps of:
means for generating first and second modulation signals having equal frequencies and having a first phase difference of substantially 90°;
means for irradiating a first electromagnetic wave of a first wavelength into said sample under control of said first modulation signal;
means for irradiating a second electromagnetic wave of a second wavelength different from the first one into said sample under control of said second modulation signal;
means for receiving electromagnetic waves of both wavelengths which have passed through said sample;

means for demodulating signals representative of the received electromagnetic waves by multiplying the same with a first sinusoidal demodulation signal and with a second sinusoidal demodulation signal having the first phase difference with respect to said first sinusoidal signal, said first and second sinusoidal demodulation signals having an identical frequency as said first and second modulation signals, such as to generate a first and a second demodulated signal; and means for analyzing said demodulated signals taking into account a system phase shift.

51. Apparatus according to claim 50, wherein said means for analyzing comprises:

means for determining said system phase shift; and means for correcting said demodulated signals on the basis of said determined system phase shift.

52. Apparatus according to claim 50, wherein said means for analyzing comprises:

means for determining the system phase shift;

means for calculating a matrix [C] based on the system phase shift according to $$[C] = \begin{bmatrix} \cos\phi & -\sin\phi \\ \sin\phi & \cos\phi \end{bmatrix};$$

means for calculating an inverse matrix $[C]^{-1}$ based on the matrix [C];

means for determining an output vector $$[L] = \begin{bmatrix} L_R \\ L_{IR} \end{bmatrix}$$

based on the amplitudes $L_R$, $L_{IR}$ of the demodulated signals; and means for calculating a corrected output vector $[A]=[C]^{-1} \cdot [L]$.

53. Apparatus according to claim 50, wherein said means for determining said system phase shift comprises:

means for reducing an amplitude of one of the first and second electromagnetic waves;

means for measuring of amplitudes of the first and second demodulated signals; and means for determining the system phase shift on the basis of the measured amplitudes of the first and the second demodulated signal.

54. Apparatus according to claim 53, wherein said means for reducing of the amplitude of one of the first and second electromagnetic waves comprises means for turning off the amplitude of this electromagnetic wave.

55. Apparatus according to claim 50, wherein said means for determining said system phase shift comprises:

means for reducing the amplitude of one of the first and second electromagnetic waves; and means for determining the difference in a zero-crossing between the received electromagnetic waves and the other of the first and second electromagnetic waves.

56. Apparatus according to claim 50, wherein the frequency of said first and second modulation signals is basically f=275 Hertz.

57. Apparatus according to claim 50, wherein said first and second modulation signals are square-wave signals.

58. Apparatus according to claim 50, wherein said first and second modulation signals are sinusoidal signals.

59. Apparatus according to claim 50 comprising a low pass filter through which the demodulated signals are fed.

60. Apparatus according to claim 50 comprising a band-filter connected between said means for receiving electromagnetic waves and said demodulating means.

61. Apparatus according to claim 50, wherein said electromagnetic waves are waves selected from the visible and/or the adjoining spectra of light.

62. Apparatus according to claim 50, wherein said apparatus is a pulse oximeter, and said medical parameter is oxygen saturation.

63. Apparatus according to claim 50, wherein said irradiating means are light-emitting diodes.

64. Method according to claim 50, wherein said electromagnetic waves are selected from red or infra-red light.

65. Apparatus for measuring medical parameters of a patient by irradiation of electromagnetic waves into a sample and for measurement and subsequent analysis of the electromagnetic waves which have passed through said sample, said apparatus comprising:

means for generating first and second modulation signals having equal frequencies and having a first phase difference of substantially 90°;

means for irradiating a first electromagnetic wave of a first wavelength into said sample under control of said first modulation signal;

means for irradiating a second electromagnetic wave of a second wavelength different from the first one into said sample under control of said second modulation signal;

means for receiving electromagnetic waves of both wavelengths which have passed through said sample;

means for generating delayed received electromagnetic waves by adding a phase shift to the received electromagnetic waves which yields, together with a system phase shift, a total phase shift of the received electromagnetic waves relative to the first and second electromagnetic waves of substantially an integral multiple of 360°;

means for demodulating signals representative of the delayed received electromagnetic waves by multiplying the same with a first sinusoidal demodulation signal and with a second sinusoidal demodulation signal having the first phase difference with respect to said first sinusoidal signal, said first and second sinusoidal demodulation signals having an identical frequency as said first and second modulation signals, such as to generate a first and a second demodulated signal; and means for analyzing said demodulated signals.

66. Apparatus according to claim 65, comprising a digital all pass filter comprising programmable filter constants for adding said phase shift to the received electromagnetic waves.

67. Apparatus according to claim 65, further comprising:

means for reducing an amplitude of one of the first and second electromagnetic waves;

means for measuring of amplitudes of the first and second demodulated signals;

means for determining the system phase shift on the basis of the measured amplitudes of the first and second demodulated signals; and means for adjusting the phase shift to yield together with the system phase shift a phase shift of an integral multiple of 360°.

68. Apparatus according to claim 65, wherein said means for reducing an amplitude of one of the first and second electromagnetic waves comprises means for turning off the amplitude of this electromagnetic wave.

69. Apparatus according to claim 65, wherein the frequency of said first and second modulation signals is basically f=275 Hertz.

70. Apparatus according to claim 65, wherein said first and second modulation signals are square-wave signals.

71. Apparatus according to claim 65, wherein said first and second modulation signals are sinusoidal signals.

72. Apparatus according to claim 65 comprising a low pass filter through which the demodulated signals are fed.

73. Apparatus according to claim 65 comprising a band-filter connected between said means for receiving electromagnetic waves and said demodulating means.

74. Apparatus according to claim 65, wherein said electromagnetic waves are waves selected from the visible and/or the adjoining spectra of light.

75. Apparatus according to claim 65, wherein said apparatus is a pulse oximeter, and said medical parameter is oxygen saturation.

76. Apparatus according to claim 65, wherein said irradiating means are light-emitting diodes.

77. Method according to claim 65, wherein said electromagnetic waves are waves selected from red or infra-red light.

* * * * *